(12) United States Patent
Escobar-Ruiz

(10) Patent No.: US 9,372,176 B2
(45) Date of Patent: Jun. 21, 2016

(54) ULTRASONIC INSPECTION METHOD

(71) Applicant: ROLLS-ROYCE PLC, London (GB)

(72) Inventor: Edwill Alejandro Escobar-Ruiz, Derby (GB)

(73) Assignee: ROLLS-ROYCE PLC, London (GB)

( * ) Notice: Subject to any disclaimer, the term of this patent is extended or adjusted under 35 U.S.C. 154(b) by 289 days.

(21) Appl. No.: 14/183,943

(22) Filed: Feb. 19, 2014

(65) Prior Publication Data

US 2014/0260625 A1 Sep. 18, 2014

(30) Foreign Application Priority Data

Mar. 13, 2013 (GB) .................................... 1304507.5

(51) Int. Cl.
*G01N 29/04* (2006.01)
*G01N 29/44* (2006.01)
(Continued)

(52) U.S. Cl.
CPC ............ *G01N 29/4454* (2013.01); *G01N 29/07* (2013.01); *G01N 29/11* (2013.01); *G01N 29/4472* (2013.01); *G01N 2291/044* (2013.01); *G01N 2291/2693* (2013.01)

(58) Field of Classification Search
CPC .......... G01N 29/4454; G01N 29/4472; G01N 29/07; G01N 29/11; G01N 29/22; G01N 29/28; G01N 29/42; G01N 29/44; G01N 29/4418; G01N 29/4436; G01N 29/4445; G01N 29/346; G01N 29/348
USPC ............ 73/588, 584, 597, 590, 592, 593, 602
See application file for complete search history.

(56) References Cited

U.S. PATENT DOCUMENTS 3,934,458 A * 1/1976 Beretsky ............ G01N 29/0645
73/602
4,651,568 A * 3/1987 Reich ..................... G01N 29/11
73/612

(Continued)

FOREIGN PATENT DOCUMENTS

| CN | 102590344 A | 7/2012 |
| JP | A-63-103963 | 5/1988 |
| JP | A-10-253599 | 9/1998 |

OTHER PUBLICATIONS

Escobar-Ruiz et al., "Ultrasonic NDE of Titanium Diffusion Bonds using Signal Phase", *The 39th Annual Review of Progress in Quantitative Nondestructive Evaluation*, 2013, pp. 1409-1416.

(Continued)

*Primary Examiner* — Helen Kwok
(74) *Attorney, Agent, or Firm* — Oliff PLC

(57) ABSTRACT

An ultrasonic inspection method for inspecting a first article. The method includes, in a first inspection process: measuring the distance between a first surface of the first article and a nominal axis at three or more measurement locations along the axis of the surface; using the measured distances to produce a mathematical model of the surface of the first article; transmitting an ultrasonic wave from a first side of the first article through the first surface of the first article at a plurality of inspection locations along the axis of the first surface, and receiving a transmitted waveform which has passed through at least part of the first article; using the model to normalize each transmitted waveform at each inspection location to the nominal axis; and identifying a signature signal from the normalized transmitted waveform at each inspection location.

18 Claims, 7 Drawing Sheets

(51) Int. Cl.
*G01N 29/07* (2006.01)
*G01N 29/11* (2006.01)

(56) References Cited

U.S. PATENT DOCUMENTS

| | | | | |
|---|---|---|---|---|
| 5,038,615 A | * | 8/1991 | Trulson | G01B 17/025 367/100 |
| 5,143,072 A | * | 9/1992 | Kantorovich | G01H 5/00 600/437 |
| 5,214,251 A | * | 5/1993 | Orban | E21B 21/08 181/102 |
| 5,225,148 A | * | 7/1993 | Desruelles | G01B 17/025 324/229 |
| 5,303,590 A | * | 4/1994 | Modderman | G01N 29/07 73/588 |
| 5,408,881 A | * | 4/1995 | Piche | G01N 29/07 73/582 |
| 5,663,502 A | * | 9/1997 | Nagashima | G01B 17/025 702/171 |
| 5,974,886 A | * | 11/1999 | Carroll | G01B 17/025 73/1.82 |
| 6,250,159 B1 | * | 6/2001 | Kreier | G01N 29/07 73/602 |
| 6,378,375 B1 | * | 4/2002 | Kobayashi | G01N 29/09 73/600 |
| 6,415,665 B1 | * | 7/2002 | Gilmore | B29C 47/92 425/169 |
| 6,494,097 B1 | * | 12/2002 | Shihadeh | A61B 8/0858 600/438 |
| 7,204,129 B2 | * | 4/2007 | Basir | G01N 29/024 73/54.01 |
| 7,933,027 B1 | * | 4/2011 | Roth | G01B 11/0625 356/27 |
| 9,134,278 B2 | * | 9/2015 | Klopffer | F16L 11/083 |

OTHER PUBLICATIONS

Search Report issued in British Application No. GB1304507.5 issued May 30, 2013.

* cited by examiner

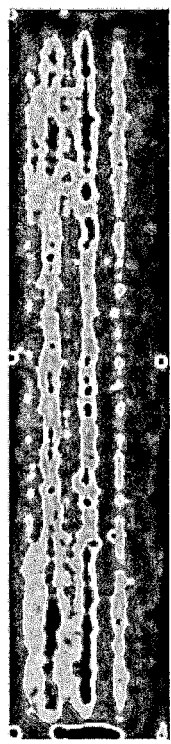 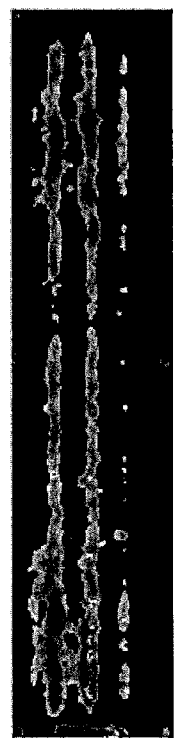
FIG. 3a  FIG. 3b
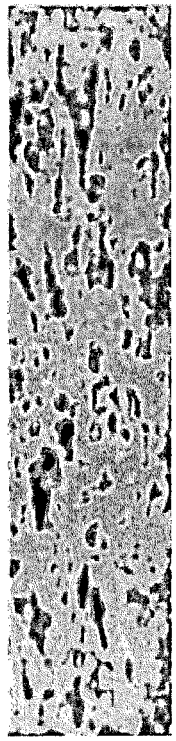 
FIG. 4a  FIG. 4b

ULTRASONIC INSPECTION METHOD

FIELD OF THE INVENTION

The present invention relates to an ultrasonic inspection method, particularly though not exclusively to an ultrasonic inspection method for detecting defects in diffusion bonded articles.

BACKGROUND TO THE INVENTION

Non-Destructive Evaluation (NDE) methods are used to detect defects within articles without damaging the articles themselves. In particular, several methods are known for inspecting bonds such as welds between joined components. In such welds, defects may comprise unbonded regions or inclusions. One such method is ultrasonic inspection.

In ultrasonic inspection, an ultrasonic wave is produced by a transducer and transmitted through a medium to the article to be inspected. In a single sided inspection, the transducer transmits an ultrasonic wave, which is then reflected back to the transducer by deformities or discontinuities in the structure of the article. These reflected signals can be used to indicate that a void is present within the bond, by for example comparing the amplitude of the transmitted and reflected waves.

In articles comprising anisotropic materials however, such as diffusion bonded titanium alloy, the diffusion bond interface can act as a weak reflector. This is because in anisotropic materials, the speed of sound in the material is dependent on the direction of travel of the sound wave relative to the crystallographic orientation of the material. In some materials, such as titanium alloy, the crystals often form macroscopic "colonies" of crystals having a similar orientation up to several millimeters in size. FIG. 1 shows a typical diffusion bond interface 12 in an article 10 comprising anisotropic Ti-6Al-4V alloy. The different shadings represent crystals having different crystallographic orientations. The bond interface 12 will act as a weak planar reflector due to the different crystallographic orientations above and below the bond interface 12. An ultrasonic wave 14 will therefore be at least partly reflected by the bond interface 12.

Consequently, an amplitude based single sided ultrasonic inspection of the bond interface 12 will result in a spurious indication of a bond defect. FIGS. 3a, 4a and 5a show amplitude based single sided ultrasonic inspections of first, 10a, second 10b and third 10c articles. In general, lightly shaded parts of FIGS. 3a-5a represent high amplitude return signals, which would generally be interpreted as defects. As can be seen, each of the inspected articles 10a, 10b, 10c would "fail" an amplitude based single sided ultrasonic inspection due to the perceived defects.

One method of overcoming this above problem is to use a two sided ultrasonic inspection method. Such a method is described in "Ultrasonic Non-destructive Evaluation of Titanium Diffusion Bonds" by K Milne et al, J Nondestruct Eval (2011) 30:225-236.

The method described in Milne et al comprises two single sided inspections performed from either side of the article at a plurality of inspection locations. The resulting reflected waveforms from each side are acquired using conventional ultrasonic inspection equipment. They need not be acquired simultaneously, but each inspection location must be known so that the corresponding pair of waveforms from each side from can be spatially related to the other at a corresponding location. These waveforms are then transferred to a suitable computer where spectral (Fourier) analysis is performed in order to establish the phases of the diffusion-bond signals within the waveforms performed from the first side and the diffusion-bond signals within waveforms performed from the second side. The two diffusion-bond signal phases acquired at each scan position are compared, and this comparison yields information about the quality of the bond. In the method described by Milne, phase differences of 180° are taken to be 'natural' differences that occur due to the acoustic impedance mismatch of the grain colonies either side of the bond. However, phase differences tending towards quadrature (90° or 270°) are indicative of a reduction in interfacial stiffness. A double-sided inspection can be performed on the principle that the 'natural' acoustic impedance mismatches are always asymmetric about the diffusion bond plane: i.e. if the phase is x° for the signal taken from the first side, then the phase of the signal taken from the second side will be x+180°. However, phase differences that result from unfavourable conditions at the diffusion bond (such as defects, lack of bonding or inclusions etc.) are always symmetric about the diffusion bond plane: the phase contribution from the unfavourable condition will be the same in the signals from both sides. We can therefore eliminate the 'natural' contribution, leaving only that which results from unfavourable conditions.

It should be noted that a captured waveform will contain several signals, one of which is the diffusion-bond signal. Other signals could for example comprise material anisotropies or bulk material defects. When performing an ultrasonic inspection, other signals can be considered to represent noise. It is therefore necessary to identify the diffusion bond signal within each waveform from each inspection location, so that the spectral analysis can be performed on the correct signal. One conventional method for identifying the diffusion bond signal from the captured waveform is known as "gating". The amplitude of each waveform is monitored until a predetermined threshold amplitude is breached, usually the echo from the top surface nearest the transducer, since this is often the largest signal in a waveform. Once the predetermined threshold amplitude is breached a fixed delay (determined by the thickness of the first component 18 in the article 10) is added to the time of the breach. The waveform between this new point and the end of the predetermined period of time has elapsed is taken to be the diffusion bond signal. The method is then repeated for the waveform taken from the other side for each inspection location.

However, this method requires access to both sides of the article in order to obtain the waveforms, preferably normal to the plane of the diffusion bond 12. In many cases this is not possible—for example, where the article to be inspected comprises the compressor bladed ring (known in the art as a "bling") of a gas turbine engine, as shown in FIG. 2. The two-sided inspection technique described above is also relatively inaccurate, since the above described method results in an inaccurate identification of the spatial location of the waveforms (i.e. in relation to the plane of the bond), and the depth of the diffusion bond signals within the respective waveforms. Consequently, some articles having insufficient bond strength will "pass" the prior two-sided inspection techniques, while some articles having sufficient bond strength will "fail", i.e. the prior methods provide both "false positives" and "false negatives".

SUMMARY OF THE INVENTION

According to a first aspect of the present invention, there is provided a method of inspecting a first article, the method comprising, in a first inspection process:

determining the distance between a first surface of the first article and a nominal axis of a transducer arrangement at three or more measurement locations along the nominal axis;

using the determined distances to produce a mathematical model of the first surface of the first article;

using the transducer arrangement to transmit a first ultrasonic wave from a first side of the first article through the first surface of the first article at a plurality of inspection locations along the nominal axis, and receiving a first transmitted waveform which has passed through the first surface;

using the model to normalise each first transmitted waveform at each inspection location to the nominal axis; and identifying a first signature signal from the first normalised transmitted waveform at each inspection location.

Advantageously, the invention provides a method of inspecting an article, for example an article comprising an ultrasonically anisotropic material, which only requires access to one side of the article, and is more accurate than previous methods. The invention relies on the discovery that variations in the geometry of the first surface of the article (i.e. variations in the distance between the article and the nominal axis of the transducer arrangement at points along the nominal axis) introduces errors when comparing transmitted waveforms from different inspection locations along the nominal axis to identify the signature signal, which in turn introduces errors when identifying defects in the article. By normalising each transmitted ultrasonic waveform from each inspection location to the nominal axis using a model derived from measurements of the surface of the article, a more accurate assessment of the transmitted waveforms can be made, and therefore a more accurate identification of the signature signals can be made.

The first article may include a bond surface disposed on a generally opposite side to the first surface. The first signature signal may comprise a back reflection signal originating from the bond surface. The method may comprise a bonding step subsequent to the first inspection process comprising bonding the bond surface of the first article to a second article having a first surface and a bond surface by a bonding process, such that a bond interface region is provided at the respective bond surfaces of the first and second articles. The bonding step may comprise a solid state bonding process, such as a diffusion bonding process.

The method may comprise a second inspection process subsequent to the bonding step, the second inspection process comprising:

using the transducer arrangement to transmit a second ultrasonic wave through the first surface of the first article at a plurality of inspection locations along the first surface of the first article, and receiving a second transmitted waveform from the bond interface region;

using the model to normalise each second transmitted waveform at each inspection location to the nominal axis;

identifying a second signature signal from the second normalised transmitted waveform at each inspection location; and comparing the first signature signal to the second signature signal to characterise the bond interface region.

By inspecting the first article prior to the bonding step, and subsequently inspecting the bond interface region, the bonded article can be inspected from only one side. This allows inspection of the article where access to the other side is not available, and increases accuracy of the inspection even where access to the other side would be available. The normalisation of the transmitted waveforms to the same nominal axis allows the waveforms from the inspection locations to be compared, such that a comparison of the signature signals from each inspection can be made.

Alternatively, the first article may comprise a bonded article having a second surface disposed generally opposite the first surface, and a bond interface region within the first article between the first and second surfaces.

Where the first article comprises a bonded article having a second surface, the method may comprise a second inspection process subsequent to the first inspection process, the second inspection process comprising:

using the transducer arrangement to transmit a second ultrasonic wave through the second surface of the first article at a plurality of inspection locations along the second surface of the first article, and receiving a second transmitted waveform from the bond interface region;

using the model to normalise each second transmitted waveform at each inspection location to the nominal axis;

identifying a second signature signal from the second normalised transmitted waveform at each inspection location; and comparing the first signature signal to the second signature signal to characterise the bond interface region.

The model of the surface of the first or second article may comprise a polynomial equation, and may comprise a second order polynomial equation. Where the polynomial equation comprises a second order polynomial equation, the equation may be of the form:

$$y=ax^2+bx+c$$

Where x represents the distance along the nominal axis, y represents the distance between the first surface of the article and the nominal axis at location x, and a, b and c are constants.

The values of a, b and c may be determined by a curve fitting algorithm which determines the values from the measured distances at each of the plurality of measurement locations.

The distance between the first surface of the article and the nominal axis may be determined by transmitting an ultrasonic wave to the first surface and detecting a reflected ultrasonic wave, and may be determined by comparing a reflected wave from a first measurement location to a reflected wave from a second measurement location.

The measurement locations and/or the inspection locations may be located at predetermined positions on a 1 dimensional or 2 dimensional array corresponding to the first surface of the first article.

The step of identifying one or both of the first and second signature signals from the first and second normalised transmitted waveforms may comprise comparing the respective normalised transmitted waveforms from a plurality of inspection locations within the array, and identifying the location of a common signal in the plurality of waveforms. The common signal may be identified by averaging the waveforms from the plurality of inspection locations and identifying a region or point of the waveform which has an energy greater than a threshold value or is at a maximum.

Since the waveforms from different locations are normalised to the nominal axis, the signature signal can be expected to be located at the same depth (i.e. at the same region of the waveform) at each normalised inspection location, i.e. at the same temporal location in each waveform. On the other hand, the depth (and so time within the waveform) of the noise would be expected to have a random distribution within the waveform. Consequently, by averaging the normalised waveforms at different locations, the noise will be cancelled, and the signal will be substantially unaltered, and can therefore be identified from the noise.

The step of identifying one or both of the first and second signature signals from the normalised transmitted waveforms may further comprise defining an extraction function comprising a time region of the respective waveforms centered on the location of the common signal. The extraction function may have an extent approximately equal to or less than the 'packet' or pulse duration of the transmitted ultrasonic wave. The first and second signature signals may comprise the portion of the respective waveforms located within the extraction function.

By using an extraction function having an extent less than the packet or pulse duration of the ultrasonic wave, the analysis of the signal can be performed only on the part of the normalised transmitted waveforms having the most energy, thereby resulting in greater accuracy of the location of the bond region.

The method may further comprise determining a phase spectrum of each signature signal at each inspection location. The step of determining a phase spectrum of each signature signal at each inspection location may comprise performing a Fourier analysis on the respective signature signal, such as a fast Fourier transform, to define a transformed signal having real and imaginary components. The method may further comprise determining the phase between the real and imaginary components of the transformed signal to provide the phase spectrum of each signature signal.

The method may further comprise determining a true phase angle $\Phi$ of each phase spectrum. The true phase angle $\Phi$ may be determined by identifying a linear region of the phase spectrum of the respective signature signal around a transducer centre frequency, and extrapolating this to the zero-frequency axis, as described in Instanes, G., A., Toppe, M., Nagy, P. (2009) Constant Group Velocity Ultrasonic Guided Wave Inspection for Corrosion and Erosion Monitoring in Pipes. Review of Progress in Quantitative Nondestructive Evaluation, 28, 1386-1393, incorporated herein by reference.

The method may further comprise identifying an extraction point within the signature signal having a minimum phase derivative, i.e. the location at which the derivative of the true phase $\Phi$ of the respective signature signal with respect to frequency is a minimum. By identifying the portion of the signal having a minimum phase derivative within the phase spectrum, a unique frequency-selected portion of the signal can be identified for each inspection location. The phase of the signal from the bond region or the back portion of the article can thereby be computed more accurately compared to prior methods. For example, it is thought that the signal phase can be obtained with at least a factor of three less error, or possibly up to an order of magnitude less error compared to the method disclosed in Milne et al. The normalisation of the waveform permits sufficient accuracy to allow an extraction function shorter than the 'packet' or pulse duration to be used, and in turn allows (via phase derivative minimisation) properties within the bond signal to be identified to a significantly greater accuracy, thereby increasing the accuracy of the inspection substantially.

The method may comprise storing the true phase angle of the first signature signal at the extraction point in a reference array, and storing the true phase angle of the respective second signature signal at the extraction point in a diffusion bond array. The step of comparing the first and second signature signals may comprise subtracting the diffusion bond array from the reference array to provide a subtracted array.

The true phases stored in the subtracted array may be used to determine an interfacial stiffness of the bond interface region. By determining the interfacial stiffnesses of the bond interface region subsequent to the bonding step, the quality of the bond can be determined, since, in general, it has been found that bond interface regions having a relatively high interfacial stiffness indicate a good quality bond, free of bond defects.

The interfacial stiffness of each inspection location in the bond interface region may be determined according to the following equation:

$$\kappa \approx \frac{\omega Z}{2\eta \tan \Phi}$$

where $\kappa$ denotes the interfacial stiffness, $\omega$ denotes the centre frequency of the transmitted ultrasonic wave, $\eta$ denotes the relative acoustic impedance mismatch $(Z_2-Z_1)/(Z_2+Z_1)$, and $\Phi$ denotes the true phase stored in the subtracted array.

BRIEF DESCRIPTION OF THE DRAWINGS

FIGS. 3a, 4a and 5a show results from prior two sided inspections of the article of FIG. 1;

FIGS. 3b, 4b and 5b show results from an inspection according to the method of the present invention;

DETAILED DESCRIPTION

Figure 2:
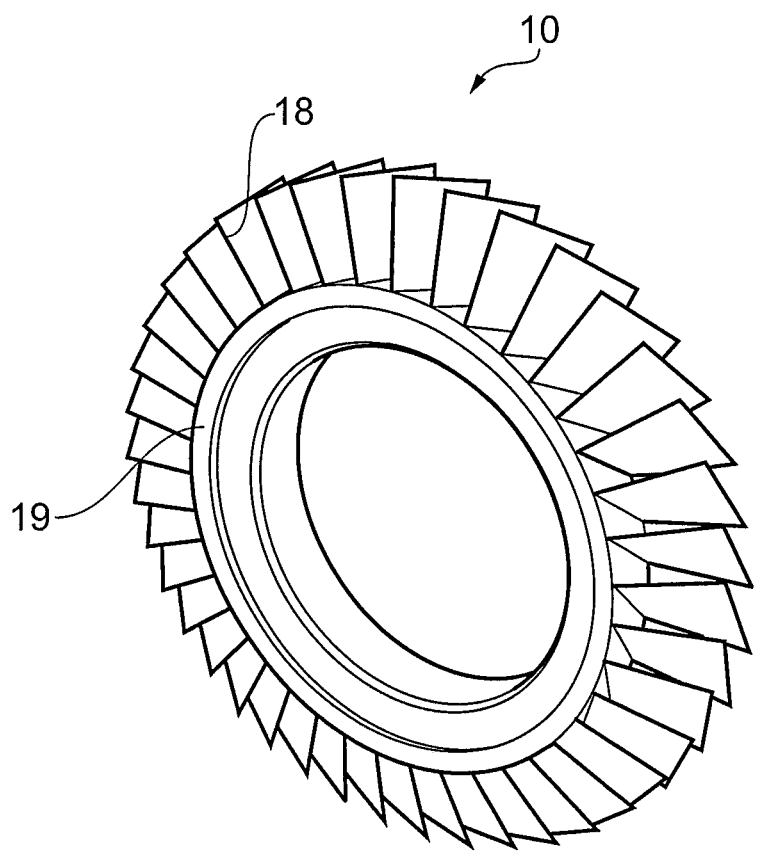
FIG. 2 shows a perspective view of a diffusion bonded bladed disc for a gas turbine engine.

FIG. 2 shows an article 10 in the form of a compressor bling for a gas turbine engine. The bling comprises a plurality of blades 18 joined to a ring 19 by a solid-state bonding process such as linear friction welding at a bond interface region 12. Linear friction welding is a known solid state method, in which articles such as a blade 18 and ring 19 are displaced relatively to one another, thereby generating heat, such that the materials at the interface between the articles diffuse into one another. Another suitable method of solid state bonding comprises diffusion welding, in which high pressure and temperatures are applied to the articles to be bonded such that the atoms of the articles diffuse into one another. Still further solid state bonding techniques are also known to the skilled person, such as electromagnetic pulse welding.

Both the blade 18 and the ring 19 of the article 10 comprise an anisotropic metallic material such as Ti-6Al-4V alloy. In the example shown in FIG. 1, the bling 10 may further comprise a metal matrix composite component 11, which is bonded to the ring 19 by a further solid-state bonding process.

Figure 1:
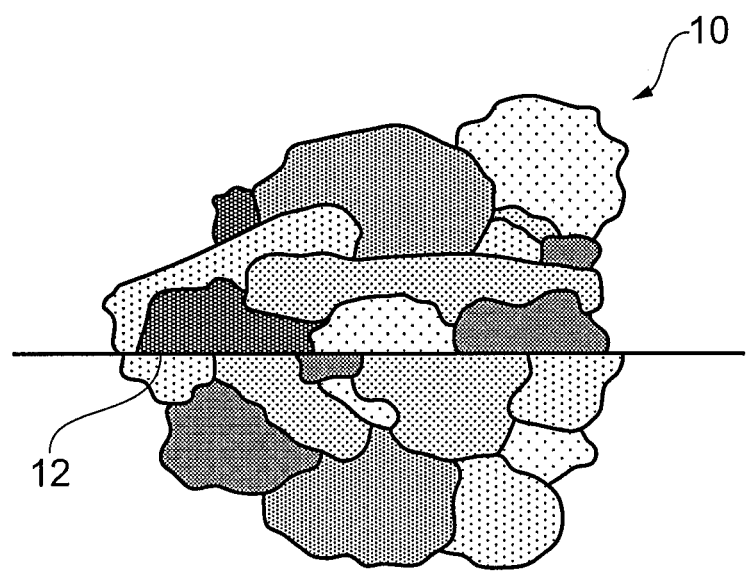
FIG. 1 shows a cross sectional view through an article comprising an anisotropic material.

FIG. 1 shows the bond interface region 12 in more detail. As can be seen, in this case, the article 10 is formed of a plurality of crystals. The darkness of each crystal represents the crystallographic orientation of the respective crystal. Due to the change in crystallographic orientation at the bond interface, traditional amplitude based inspections of the article 10 will result in large amplitude readings at the bond interface region 12, regardless of whether the bond interface region comprises defects, or is substantially free of defects.

Figure 7A:
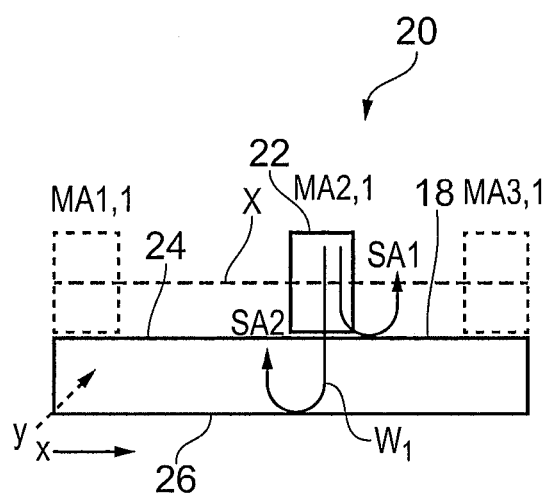
FIGS. 7a and 7b show a diagrammatic representation of a first step and a second step respectively of a single sided inspection method.
Figure 7B:
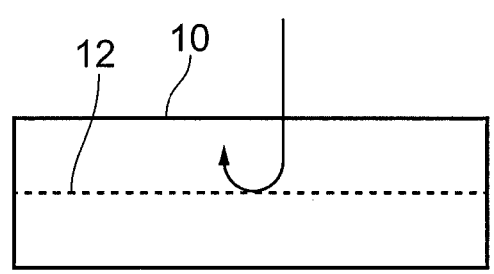

Referring to FIGS. 7a and 7b, in a first embodiment, the article 10 is inspected to characterise the quality (i.e. the presence or absence of bond defects) of the bond interface region 12 according to the following method.

In a first step, prior to bonding of the components (such as component 18) of the article 10, one of the components of the article 10 (e.g. the blade 18 or the disk 19) is immersed into a liquid bath, such as a water bath 20.

An ultrasonic transducer 22 is placed in the water bath 20 adjacent or in contact with a first surface 24 of the component 18 at a first measurement location MA1,1 along the first surface 24. A first ultrasonic wave WA1,1 is transmitted into the component 18 in a direction generally normal to the first surface 24, toward a generally opposite second surface 26. The first ultrasonic wave WA1,1 has a frequency suitable for ultrasonic inspection of the material of the component. In one example, the ultrasonic wave has a centre frequency of approximately 10 MHz where the component comprises titanium alloy. Relatively broadband transducers are preferable, which produce a range of frequencies such as 2 to 30 MHz. The component 18 and transducer 22 are arranged within the water bath 20 such that the second surface 26 corresponds to the bonding region 12 when the components 18, 19 are bonded.

Part of the wave WA1,1 is reflected by the first surface 24. The reflected wave from the first surface 24 is recorded by in computer memory (not shown) electrically connected to the transducer 22.

Once the reflected ultrasonic wave WA1,1 has been recorded, the transducer is moved along a nominal axis X of the transducer arrangement to a second measurement location MA2,1 as shown in FIG. 7a. A second ultrasonic wave WA2,1 is then transmitted through the component 18, and is reflected off the first surface 24 at the second measurement location MA2,1. The reflected waveform is recorded in memory. A third ultrasonic wave WA3,1 is then transmitted through the component 18 at a third measurement location MA3,1. Further waves WAx,1 may also be taken at further measurement locations MAx,1 along the surface 24 of the component 18.

Further ultrasonic waves WAx,y may be transmitted through the component 18 at measurement locations MAx,y at distances along a nominal axis Y normal to the nominal axis X and substantially parallel to the first surface 24, as shown in FIG. 7a. The data from the reflected ultrasonic waves WAx,y, are stored in a reflected wave array in computer memory.

The reflected waves WAx,y from the first surface 24 at each measurement location MAx,y are used to determine the distance of the first surface 24 from the nominal axes X,Y normal to the nominal axes X,Y at each measurement location MAx,y. This is achieved by comparing the reflected waves from the first surface 24 at each measurement location MAx,y, and using a cross-correlation algorithm to find the depth within the waveform at which a first surface reflection signal SA1 from the reflected waveform from each location MAx,y is received by the transducer 22. The distance of the first surface 24 at each measurement location MAx,y can thereby be calculated from this time, by dividing the known speed of the waves in the component 18 by the time at each location MAx,y.

The distances are then used to form a model of the first surface 24 for the X and Y axes. For example, for a curved surface in the axis X, the model could comprise a quadratic equation in the form:

$$y = ax^2 + bx + c$$

Where x represents the distance of the transducer 22 along the nominal axis X, y represents the distance between the first surface 24 of the component 18 and the nominal axis X at distance x, and a, b and c are constants derived from the measured distances at the locations MAx,y. The constants a, b and c may be derived by a curve fitting algorithm. An equivalent function is used for the Y axis. For components having more complex surface shapes, a different model may be used to describe the first surface 24.

Part of the ultrasonic waves WAx,y transmitted by the transducer 22 at each measurement location MAx,y penetrates the first surface 24 of the component 18, is transmitted therethrough, and reaches the second surface 26. At least a part of the transmitted wave WAx,y is then reflected due to the difference in acoustic impedance between the component 18 and the water in the water bath 20. The reflected transmitted wave WAx,y then travels through the component 18 again, exits the first surface 24, and is detected by the transducer 22. The reflected transmitted wave therefore contains a first signature signal in the form of a second surface reflection signal SA2. The reflected wave WAx,y is recorded by the computer in the same array as the previous data, such that a continuous waveform WAx,y is recorded for each measurement location, which includes both the reflected first surface signal SA1 and a reflected second surface signal SA2, as well as further signals within the waveform WA, which can be regarded as "noise". Further ultrasonic waves WAx,y may be transmitted at inspection locations between the measurement locations, and the transmitted waveform stored in the same array (WAx, y, f(t)). However, at this stage, it is difficult to accurately identify the location of the second surface signal SA2 from within the waveform WA, since the signal SA2 is relatively weak compared to the other signals, i.e. the "signal to noise ratio" of SA2 is relatively low.

Figure 8A:
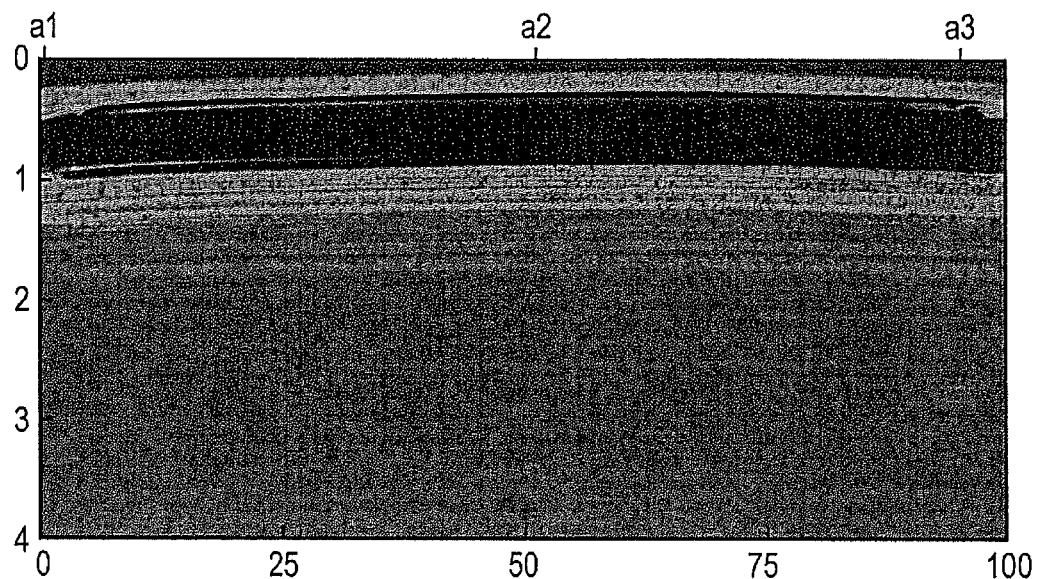
FIG. 8a shows an ultrasonic scan through a cross section of an article first article.
Figure 8B:
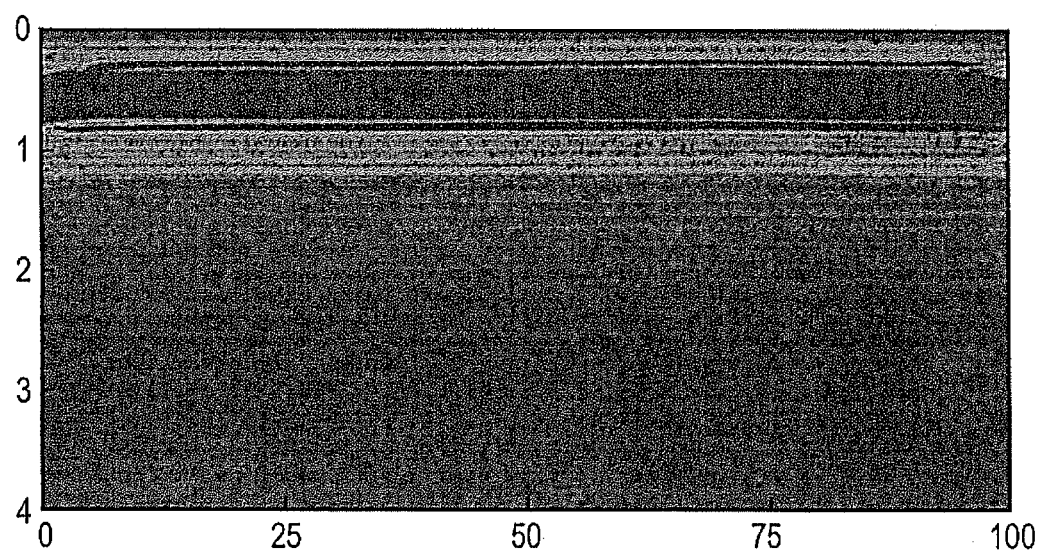
FIG. 8b shows an a normalised ultrasonic scan through a cross section of an article.

In order to identify the second surface signal SA2, the waveform for each location WAx,y in the array is then normalised to the nominal axes X,Y. The waveform is normalised by inputting the distance along the nominal axes for each location in the array, and applying the model to produce a normalised waveform WAf(x,y). FIGS. 8a and 8b respectively show the waveform before and after the normalisation. In other words, the data in the array is shifted by the distance between the surface and the nominal axis for each location in the array as determined by the model, such that the signal SA2 will be located at the same depth within the normalised waveform at each inspection location.

Figure 9A:
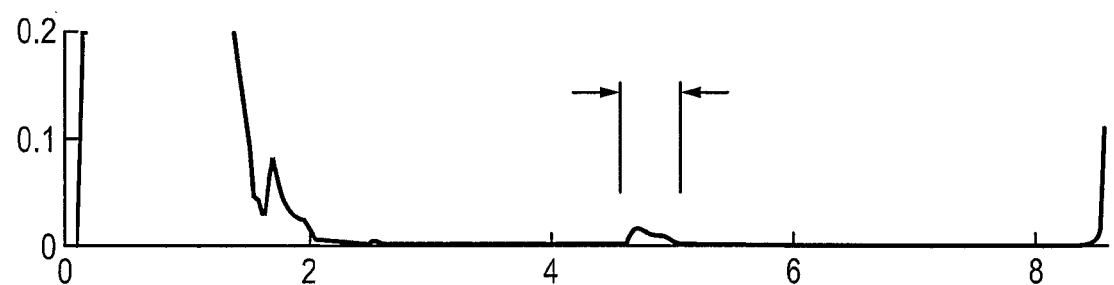
FIGS. 9a and 9b show ultrasonic waveform energy in ungated and normalised conditions respectively.
Figure 9B:
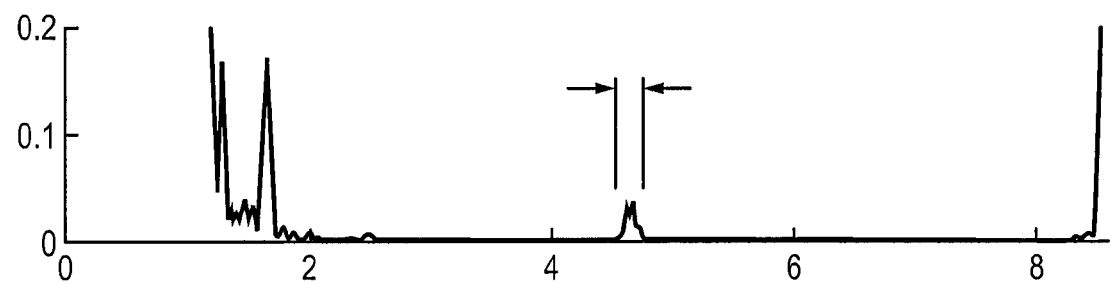

The second signal SA2 is then identified from within the normalised waveform. Since the waveforms are normalised, the second signal SA2 should be located at approximately the same depth for each inspection location. The signal SA2 location can therefore be determined by spatially averaging the normalised waveforms, i.e. by averaging the normalised waveforms from each inspection location. The spatial averaging results in a common signal, i.e. a distinct peak within the normalised, averaged waveform, as shown in FIG. 9b, whereas the noise is minimised, since the noise is randomly distributed between the different inspection locations. The approximate location of the signal SA2 can then be determined visually by a user, or can be determined automatically, by identifying a region of the waveform having energy greater than a predetermined threshold value, or by identifying the region of the waveform having the greatest energy at the depth the signal SA2 is expected to arrive at. FIGS. 9a and 9b compare the spatial averaging of a non-normalised transmitted waveform, and a normalised transmitted waveform respectively. As will be appreciated, the normalisation of the waveform results in both a more precise identification of the location of the signal SA2, and also results in a higher peak, i.e. a greater energy, which ensures a greater signal to noise ratio, and therefore more accurate characterisation of any bond defects.

Once the approximate location of the second surface signal SA2 within the normalised waveform WAf(x,y) at each inspection location (i.e. the depth of the surface signal SA2 from the first surface 24 normal to the axes X, Y) is determined as above, the signal SA2 can be analysed to determine a signature phase φ1 of the signal SA2.

Figure 10A:
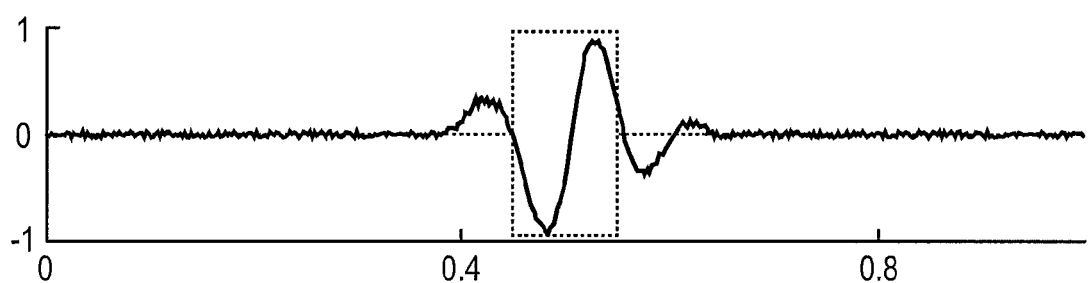
FIGS. 10a and 10b show an ultrasonic waveform with an extraction function shorter than the 'packet' or pulse duration and a conventional extraction function respectively.

In order to determine the signature phase φ1 of the signal SA2, an extraction function is defined, as shown in FIG. 10a. The extraction function comprises a time region of the normalised waveform WAf(x,y) for each inspection location centered on the location within the waveform WAf(x,y) containing the second surface signal SA2 as identified in the previous step.

Figure 10B:
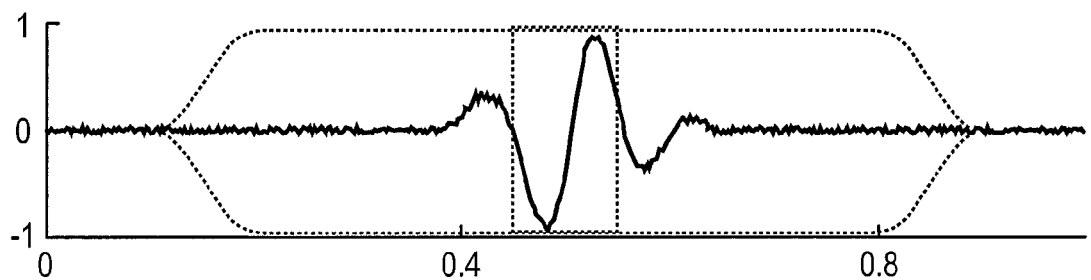

The extraction function defines the region of the waveform (also known as a "window") that is analysed to determine the properties of the signal SA2 to thereby characterise the second surface 26 of the component 18. Referring to FIG. 10a, the extraction function has a width less than the duration of the 'packet' or pulse of the transmitted ultrasonic wave, i.e. in the present invention the window has a duration equal to one cycle of the interrogating ultrasound (for a 10 MHz wave, 1 cycle=1/10 MHz=0.1 μs), and is centered on the location of the common signal. The part of the waveform located within the extraction function is taken to be the first signature signal SA2. In comparison, FIG. 10b shows a typical extraction function for a prior inspection method. As can be seen, the prior extraction function has a greater "width", i.e. a greater portion of the waveform is examined to characterise the second surface 26 of the component. Since the location of the first signature signal SA2 can be identified more accurately in the method described herein, the extraction function can be narrower, and it has been found that by having an extraction function width less than the duration of the packet of the transmitted ultrasonic wave, the first signature signal SA2 can be analysed with a high degree of accuracy.

Once the extraction function has been defined, a Fourier transform is applied to the waveform within the window, which provides magnitude H(ω) and phase φ(ω) spectra for each inspection location MAx,y.

The magnitude H(ω) can be determined according to the following equation:

$$H(\omega; t_w)e^{i\varphi(\omega;t_w)} = \int_{t_w-\frac{t_w}{2}}^{t_w+\frac{t_w}{2}} h(t)e^{-i\omega(t-t_w)}dt$$

Where t and ω denote time and angular frequency of the transducer wave respectively. The phase spectra for each inspection location can be determined according to the following equation:

$$\varphi(\omega;t_w)=\omega[t_w-s_p(\omega)z]$$

Where $s_p$ denotes the phase slowness and z denotes the propagation distance through the component 18.

The "true phase" angle φ is then calculated from each phase spectrum for each inspection location. The true phase angle φ is determined by identifying a linear region of the phase spectrum of the respective signature signal around a transducer centre frequency, and extrapolating this to the zero-frequency axis, as described in Instanes, G., A., Toppe, M., Nagy, P. (2009) "Constant Group Velocity Ultrasonic Guided Wave Inspection for Corrosion and Erosion Monitoring in Pipes" published in Review of Progress in Quantitative Nondestructive Evaluation, 28, 1386-1393, incorporated herein by reference.

An extraction point within the signal SA2 is then calculated by determining a location of the signal (i.e. a depth) having a minimum true phase angle derivative, i.e. the location at which the derivative of the true phase CD of the respective signature signal with respect to frequency is a minimum. This has been found to be the location within the signature signal SA2 at which the energy of the signature signal SA2 is greatest, and the signal to noise ratio should therefore also be greatest. This greatly increases the accuracy of the determination of the signature phase of the first signature signal SA2. The phase of the signal SA2 at the location having a minimum phase derivative represents the signature phase φ1 of the second surface 26.

Once the signature phase φ1 of the second surface 26 of the first component 18 has been identified, the first component 18 is then bonded to the second component 19 by a bonding process which bonds the second surface 26 of the first component 18 to a first surface 28 of the second component 19 to form the article 10, as shown in FIG. 7b.

In one example, the bonding process comprises a diffusion bonding process, such as a hot isostatic pressing (HIP) operation. Other types of bonding processes and in particular solid-state bonding processes can be employed. Once the article 10 is formed, the second surface 26 of the second component 19 and the first surface 24 of the first component 18 form a bond interface region 12. The bond interface region 12 may comprise defects, which can be detected by the method of the present invention.

Once the first and second components 18, 19 are bonded to form the article 10, a second ultrasonic wave WB is transmitted from the transducer 20 from the first surface 24 of the first article 18 through the bond interface region 12 using the same frequency as the first wave WA. A portion of the ultrasonic wave WB is reflected by the first surface 24. A further portion of the ultrasonic wave WB is transmitted through the first surface 24 and passes through the bond region 12, where it is in turn partially reflected back towards the transducer by the bond interface region 12 as shown in FIG. 7b.

The transducer 22 is again scanned along the X and Y axes, and records the reflected transmitted waveform WBx,y from a plurality of inspection locations forming a second array. The wave WB is again normalised using the mathematical model of the first surface 24 of the first component 18 to produce a normalised reflected wave WB. The normalised reflected wave WB is thereby aligned to the normalised transmitted wave WA for each inspection location, since both waves WA, WB are normalised to the same nominal axes X, Y. The wave WB comprises a surface reflection signal SB1 from the first surface 24 of the first component 18, and a second signature signal in the form of a bond signal SB2 from the bond interface region 12.

The bond signal SB2 is then identified from within the normalised waveform WB. The location of the bond signal SB2 is again determined by spatially averaging the normalised waveforms W2 for each inspection location, and determining the location of the waveform having a greater value than a predetermined amplitude threshold value or by seeking the maximum energy point away from that of the first surface reflection SB1.

A signature phase φ2 of the signal SB2 is then identified in a similar manner to that used to determine the signature phase φ1 of the signal SA2. The signature phase φ2 for each inspection position is stored in a second signature phase array.

The signature phases φ1 and φ2 for each corresponding position in the arrays are then subtracted from one another for each inspection location to generate a subtracted phase φ3. The subtract phase φ3 for each inspection location is stored in an array, and can be used to determine the interfacial stiffness κ of the bond region 12. The normalised phase φ3 is used to estimate the interfacial stiffness κ using the following equation:

$$\kappa \approx \frac{\omega Z}{2\eta \tan \Phi 3}$$

Where ω represents the frequency of the ultrasonic waves W1 and W2, Z is the acoustic impedance of the bonded media, and η is the relative acoustic impedance mismatch of the material of the article 10.

Figure 5A:
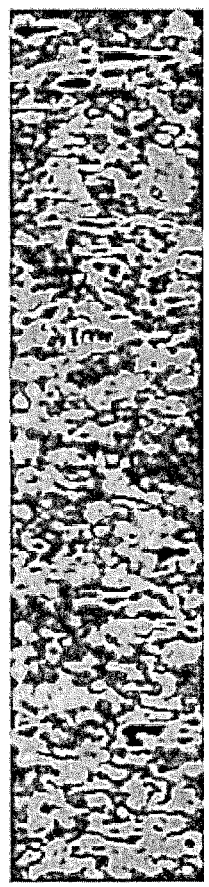
Figure 5B:
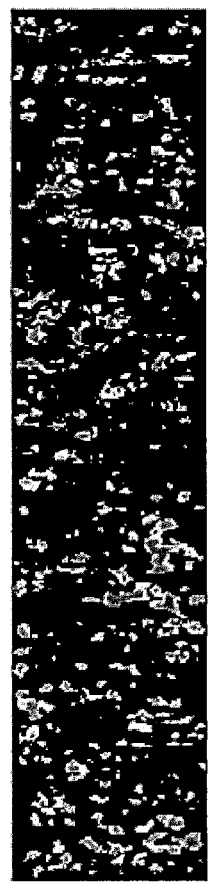
Figure 6:
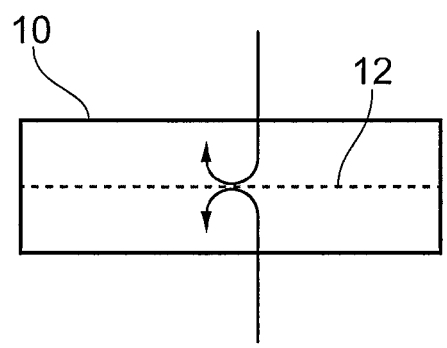
FIG. 6 shows a diagrammatic representation of a two sided inspection method.

The interfacial stiffness κ for each inspection location is then stored in an interfacial stiffness array. The quality of the bond region 12 can be assessed using the data stored in the interfacial stiffness array. In general, a lower interfacial stiffness indicates a lower quality bond at the bond interface region 12, while a higher interfacial stiffness indicates a relatively high quality bond. FIGS. 3b, 4b and 5b show interfacial stiffness maps of a first, second and third articles 10a, 10b, 10c obtained using the above described method, which diagrammatically represent the data stored within the interfacial stiffness array obtained for each article. A darker colour represents a higher interfacial stiffness. As can be clearly seen, the interfacial stiffness of articles 10a and 10c are considerably lower than the interfacial stiffness of article 10b. It can therefore be deduced that the quality of the bond of articles 10a and 10c are much lower than that of either of article 10b. Crucially, this is not apparent from conventional ultrasonic inspections (see images FIGS. 3a, 4a and 5a). The quality of the bonds of articles 10a and 10b have been corroborated experimentally, and have been found to have been consistent with the results from interfacial stiffness tests conducted according to the described method.

The invention therefore provides an ultrasonic inspection method that can identify defects in articles more accurately than prior methods. Furthermore, in some embodiments, the method can be used where access is only available from one side of the article. However, the invention is also applicable to two-sided inspections, which results in a more accurate assessment of the bond.

While the invention has been described in conjunction with the exemplary embodiments described above, many equivalent modifications and variations will be apparent to those skilled in the art when given this disclosure. For example, the first and second ultrasonic waves may be transmitted through the component after the component is bonded, from opposite sides. Accordingly, the exemplary embodiments of the invention set forth above are considered to be illustrative and not limiting. Various changes to the described embodiments may be made without departing from the spirit and scope of the invention.

The invention claimed is:

1. An ultrasonic inspection method for inspecting a first article, the method comprising, in a first inspection process:
   determining a distance between a first surface of the first article and a nominal axis of a transducer arrangement at three or more measurement locations along the axis of the surface;
   using the determined distances to produce a mathematical model of the surface of the first article;
   using the transducer arrangement to transmit a first ultrasonic wave from a first side of the first article through the first surface of the first article at a plurality of inspection locations along the nominal axis, and receiving a first transmitted waveform which has passed through the first surface;
   using the model to normalise each first transmitted waveform at each inspection location to the nominal axis; and
   identifying the location of a first signature signal from the first normalised transmitted waveform at each inspection location.

2. A method according to claim 1, wherein the first article comprises a bond surface disposed on a generally opposite side to the first surface, and wherein the first signature signal comprises a back reflection signal originating from the bond surface.

3. A method according to claim 2, wherein the method comprises a bonding step subsequent to the first inspection process, the bonding step comprising bonding the bond surface of the first article to a second article having a first surface and a bond surface by a bonding process, such that a bond is provided at the respective bond surfaces of the first and second articles.

4. A method according to claim 3, wherein the method comprises a second inspection process subsequent to the bonding step, the second inspection process comprising:
   using the transducer arrangement to transmit an second ultrasonic wave through the first surface of the first article at each of the inspection locations along the first surface of the first article, and receiving a second transmitted waveform which has passed through a bond surface of the first article;
   using the model to normalise each second transmitted waveform at each inspection location to the nominal axis;
   identifying the location of a second signature signal from the second normalised transmitted waveform at each inspection location; and
   comparing the first signature signal to the second signature signal to characterise the bond interface region.

5. A method according to claim 4, wherein the comparison of the first signal to the second signal comprises determining an interfacial stiffness of the respective bond surfaces.

6. A method according to claim 3, wherein the model of the surface of the first or second article comprises a polynomial equation of the form $y=ax^2+bx+c$, where x represents a distance along the nominal axis, y represents a distance between the first surface of the article and the distance x along the nominal axis, and a, b and c are constants.

7. A method according to claim 1, wherein the distance between the surface of the article and the nominal axis is determined by transmitting an ultrasonic wave through the first surface and detecting a reflected ultrasonic wave from the first surface.

8. A method according to claim 4, wherein the measurement locations and/or the inspection locations are located at predetermined positions on a 1 dimensional or a 2 dimensional array corresponding to the first surface of the first article.

9. A method according to claim 8, wherein the step of identifying one or both of the first and second signature signals from the respective normalised transmitted waveforms comprises comparing the normalised transmitted waveform from a plurality of inspection locations within the 1 dimension or the 2 dimensional array, and identifying the location of a common signal in the normalised transmitted waveforms.

10. A method according to claim 9, wherein the location of the common signal is identified by averaging the normalised transmitted waveforms from the plurality of inspection locations within the 1 dimensional or the 2 dimensional array and identifying a region or point of the signature signal in which the average normalised transmitted waveform has an energy greater than a threshold value or is at a maximum.

11. A method according to claim 10, wherein the identifying the signature signal from the averaged normalised transmitted waveforms further comprises defining an extraction function comprising a region of the respective average normalised transmitted waveform centered on the location of the common signal.

12. A method according to claim 11, wherein the extraction function has an extent approximately equal to or less than a cycle duration of the transmitted ultrasonic wave.

13. A method according to claim 4, further comprising determining a phase spectrum of the first or the second signature signal.

14. A method according to claim 13, wherein the determining the phase spectrum of the first or the second signature signal further comprises performing a Fourier analysis on the first or the second signature signal to provide a transformed signal, and determining a phase between real and imaginary components of the transformed signal.

15. A method according to claim 14, wherein the method comprises determining a true phase angle $\Phi$ of each phase spectrum.

16. A method according to claim 15, further comprising identifying an extraction point within the first and the second signature signals having a minimum phase derivative, and storing the true phase angle of the first signature signal at the extraction point in a reference array, and storing the true phase angle of the respective second signature signal at the extraction point in a diffusion bond array.

17. A method according to claim 16, wherein the comparing the first signature signal to the second signature signal further comprises subtracting the diffusion bond array from the reference array to provide a subtracted array, and determining an interfacial stiffness for each inspection location from the subtracted array.

18. A method according to claim 16, wherein the comparing the first signature signal to the second signature signal further comprises subtracting the diffusion bond array from the reference array to provide a subtracted array, and determining an interfacial stiffness for each inspection location from the subtracted array.

* * * * *